United States Patent [19]

Chung et al.

[11] Patent Number: 5,312,923

[45] Date of Patent: May 17, 1994

[54] PROCESS FOR PREPARING FIBRINOGEN RECEPTOR ANTAGONISTS

[75] Inventors: John Y. L. Chung, Edison; David L. Hughes, Old Bridge; Dalian Zhao, Scotch Plains, all of N.J.

[73] Assignee: Merck & Co., Inc., Rahway, N.J.

[21] Appl. No.: 17,922

[22] Filed: Feb. 16, 1993

Related U.S. Application Data

[63] Continuation-in-part of Ser. No. 843,690, Feb. 28, 1992, abandoned.

[51] Int. Cl.$^5$ ............... C07D 211/02; C07D 211/82
[52] U.S. Cl. .................... 546/185; 546/335; 546/232
[58] Field of Search ............ 546/232, 185; 548/335

[56] References Cited

FOREIGN PATENT DOCUMENTS 0478363 4/1992 European Pat. Off. .

*Primary Examiner*—Alan Siegel
*Attorney, Agent, or Firm*—Richard S. Parr; Melvin Winokur; Paul D. Matukaitis

[57] ABSTRACT

The invention is a highly efficient synthesis for making compounds of the formula:

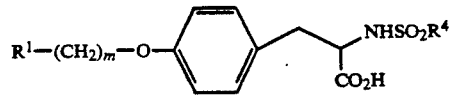

wherein:

$R^1$ is a six membered saturated or unsaturated heterocyclic ring containing one or two heteroatoms wherein the heteroatoms are N; or $NR^6$, wherein $R^6$ is H or $C_{1-10}$ alkyl;

m is an integer from two to six; and $R^4$ is aryl, $C_{1-10}$ alkyl, or $C_{4-10}$ aralkyl.

3 Claims, No Drawings

PROCESS FOR PREPARING FIBRINOGEN RECEPTOR ANTAGONISTS

CROSS-REFERENCE TO RELATED APPLICATIONS

This application is a continuation-in-part of U.S. Ser. No. 07/843,690, filed Feb. 28, 1992 now abandoned.

BACKGROUND OF THE INVENTION

European Publication 478 363 describes fibrinogen receptor antagonists which can be prepared according to the procedure of the present invention. According to the procedure described in EP 478 363, the compound:

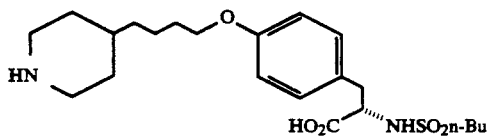

is prepared according to an 11-step procedure involving the formation of potentially hazardous NaH/DMF for ether formation, which required a chromatographic purification.

Zenitz, U.S. Pat. No. 3,124,586 and Singerman et al., *J. Heterocyclic Chem.* (1966), 3, 74, describe a procedure for preparing 4-(4-pyridinyl)butanol.

Beumel et al., *Synthesis* (1974), 43; Screttas et al., *Chimia* (1970), 109; and Osuch et al., *Chimia* (1956), 1723, describe a procedure for metallation of 4-picoline.

Barlos et al., *Liebigs. Ann. Chem.* (1986), 1407 describe Mitsunobu alkylation of tyrosine derivatives.

SUMMARY OF THE INVENTION

The invention is a highly efficient synthesis for making compounds of the formula:

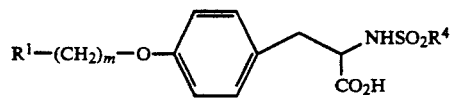

wherein:
$R^1$ is a six membered saturated or unsaturated heterocyclic ring containing one or two heteroatoms wherein the heteroatoms are N; or $NR^6$, wherein $R^6$ is H or $C_{1-10}$ alkyl;
m is an integer from two to six; and
$R^4$ is aryl, $C_{1-10}$ alkyl, or $C_{4-10}$ aralkyl.

DETAILED DESCRIPTION OF THE INVENTION

The invention is a process for preparing fibrinogen receptor antagonists of the formula:

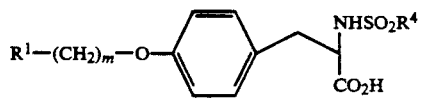

wherein
$R^1$ is a six membered saturated or unsaturated heterocyclic ring containing one or two heteroatoms wherein the hetero atoms are N; or $NR^6$ wherein $R^6$ is $C_{1-10}$ alkyl;
m is an integer from two to six; and
$R^4$ is aryl, $C_{1-10}$ alkyl, or $C_{4-10}$ aralkyl, according to the procedure whereby

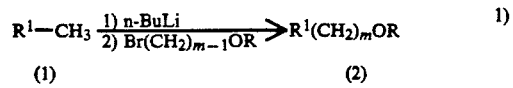

methylated $R^1$ (1) is reacted with nBuLi, before quenching with a straight chain alkyl group having Br at one end and OR at the other end, wherein R is tetrahydropyran, to yield (2);

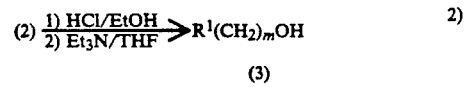

(2) is aged, first in hydrogen chloride gas in ethanol, and then neutralized in triethylamine/tetrahydrofuran, to form (3); and

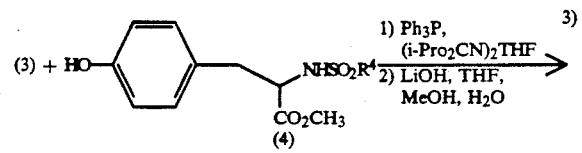

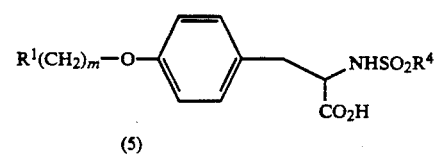

(3) is combined with (4) to yield (5) after ester hydrolysis.

Preferably, when $R^1$ is pyridine, (5) is selectively hydrogenated using Pd/C in acetic acid

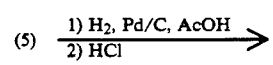

to yield

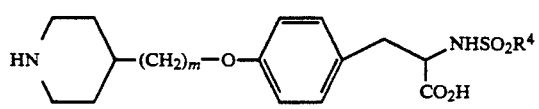

.HCl

The synthesis of the invention uses inexpensive starting materials, and employs the Mitsunobu reaction to effect the ether formation in high yield and simple purification procedure. The prior art reaction employs a potentially hazardous NaH/DMF mixture to effect the ether formation in low yield, which requires a chromatographic purification.

Preferably, the invention is a highly efficient synthesis for making

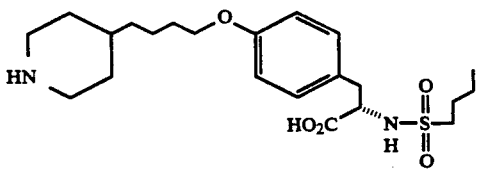

The six-step synthesis employs 4-picoline, as a latent form of piperidine, which eliminates the need for protection. O-alkylation of a tyrosine derivative under Mitsunobu condition followed by saponification of the methyl ester, extractive removal of the Mitsunobu by-products, and recrystallizations provide the coupled product in high yield and purity. Selective hydrogenation of the pyridine ring is achieved by using 10% Pd/C in AcOH at 70° C.

Fibrinogen receptor antagonists prepared according the process of the invention may be used for inhibiting the attachment of fibrinogen to the glycoprotein IIb-/IIIa receptor site. They may be administered to patients where inhibition of human or mammalian platelet aggregation or adhesion is desired.

Certain fibrinogen receptor antagonists of the invention are eliminated from circulation rapidly and are particularly useful in inhibiting platelet aggregation in situations where a strong antithrombotic of short duration or effectiveness is needed. Thus, these fibrinogen receptor antagonists may find utility in surgery on peripheral arteries (arterial grafts, carotid endaterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

The fibrinogen receptor antagonists can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount can be employed as an anti-aggregation agent.

These fibrinogen receptor antagonists may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gpIIb/IIIa on the platelet membranes and fibrinogen adsorbed to the surface of the circuit. (Gluszko et al., *Amer. J. Physiol.*, 252(H), 615-621 (1987)). Platelets released from artificial surfaces show impaired hemostatic function. The fibrinogen receptor antagonists may be administered to prevent adhesion.

Other applications include prevention of platelet thrombosis, thromboembolism and reocclusion during and after thrombolytic therapy and prevention of platelet thrombosis, thromboembolism and reocclusion after angioplasty or coronary and other arteries and after coronary artery bypass procedures. They may also be used to prevent myocardial infarction.

The dosage regimen utilizing these fibrinogen receptor antagonists is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of these fibrinogen receptor antagonists, when used for the indicated effects, will range between about 0.01 mg per kg of body weight per day (mg/kg/day) to about 100 mg/kg/day and preferably 1.0-100 mg/kg/day and most preferably 1-20 mg/kg/day. Intravenously, the most preferred doses will range from about 1 to about 10 mk/kg/minute during a constant rate infusion. Advantageously, these fibrinogen receptor antagonists may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

The fibrinogen receptor antagonists are typically administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintergrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The fibrinogen receptor antagonists can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The fibrinogen receptor antagonists may also be delivered by the use of monoclonal antibodies as individual carriers to which the fibrinogen receptor antagonists are coupled. They may also be coupled with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylsysine substituted with palmitoyl residues. Furthermore, they may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The fibrinogen receptor antagonists can also be co-administered with suitable anticoagulation agents, including antiplatelet agents such as heparin, aspirin, warfarin, dipyridamole and other compounds and agents known to inhibit blood clot formation, or thrombolytic agents such as plasminogen activators or streptokinase, to achieve synergistic effects in the treatment of various vascular pathologies.

The activity of these fibrinogen receptor antagonists is illustrated below. One test used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with these fibrinogen receptor antagonists, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2 \times 10^8$ per ml), fibrinogen (100 micrograms per ml (ug/ml)), $Ca^{2+}$ (1 mM), and the fibrinogen receptor antagonists tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

Inhibition of ADP-stimulated platelets is shown below in Table 1, which compares the concentration (dosage) of fibrinogen receptor antagonist required to inhibit aggregation by 50% relative to a control lacking the fibrinogen receptor antagonist.

TABLE 1

| Compound | $IC_{50}$ μM |
|---|---|
| (structure) | 0.015 |
| (structure) | 0.018 |
| (structure) | 0.018 |
| (structure) | 0.029 |
| (structure) | 0.063 |

EXAMPLE 1

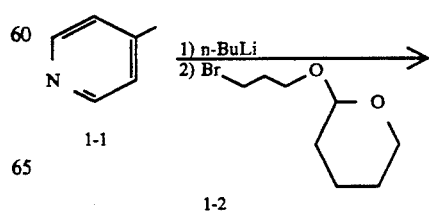

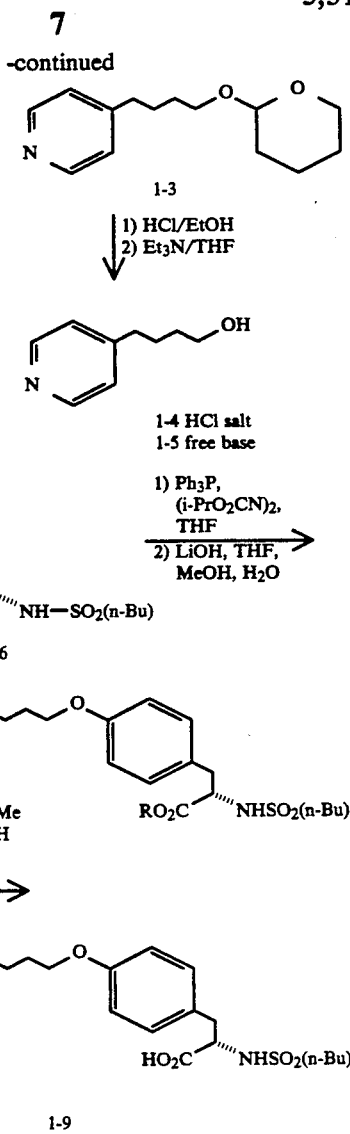

Preparation of N-n-Butanesulfonyl-(L)-tyrosine methyl ester (1-6)

A 50 L four-neck round bottom flask equipped with a mechanical stirrer, condenser, nitrogen inlet, HCl trap, heating unit and a thermometer probe was purged with nitrogen overnight and then charged with (L)-tyrosine methyl ester HCl salt (1304 g, 5.628 mol), CH$_3$CN (16 L), pyridine (994.3 g, 12.57 mol) and n-butanesulfonyl chloride (924.83 g, 5.906 mol). The mixture was heated at 65° C. for 20 h. The solvent was removed in a batch concentrator under house vacuum at 40° C. over 1–2 days. The resulting black oil was washed with 10% KHSO$_4$ (8.5 L) and the mixture extracted with methylene chloride (4×8 L). The organic was filtered through 2.9 kg MgSO$_4$ (top) and 1.3 kg flash-grade SiO$_2$ (bottom) in a sinter glass funnel. Evaporation of the filtrate gave ~1021 g solid (purity=90 A%). The solid was dissolved in toluene (5 L) with heating and the batch was aged at ambient temperature for 5 h and then filtered. The filter cake was washed with toluene (2 L) and dried to give 857.5 g (48%) of 1-6 as an off-white solid. mp 70°–71° C.; [α]$^{25}_D$=−27.0° (c 0.967, MeOH); MS(EI) m/z 315 (M+).

$^1$H NMR (CD$_3$OD) δ 7.06 (d, J=7.7 Hz, 2H), 6.72 (d, J=7.7 Hz), 4.10 (ABq, J=9.6, 5.1 Hz, 1H), 3.02 (ABq, J=13.7, 5.1 Hz, 1H), 2.73 (ABq, J=13.7, 9.6 Hz, 1H), 2.61 (t, J=7.9 Hz, 2H), 1.41 (m, 2H), 1.33 (m, 2H), 0.83 (t, J=7.2 Hz, 3H).

$^{13}$C NMR (CD$_3$OD) δ 174.1, 157.6, 131.6, 128.8, 116.3, 59.5, 54.1, 52.8, 39.0, 26.5, 22.5, 13.9. Anal. Calcd for C$_{14}$H$_{21}$O$_5$NS: C, 53.32; H, 6.71; N, 4.44. Found: C, 53.37; H, 6.86; N, 4.42.

Preparation of 4-(4-Pyridinyl)butanol (1-5)

A 12 L four-neck round bottom flask equipped with a mechanical stirrer, condenser, addition funnel with side-arm and a thermometer probe was purged with nitrogen overnight. THF (2.4 L) and 4-picoline (322.5 g, 3.46 mol) were added and the batch was cooled to −40° C. A solution of n-butyllithium (2.69 L of 1.56M solution, 4.21 mol) in hexane was added slowly while keeping the internal temperature <−30° C. The addition took about 1 h to give an orange solution with some precipitate. The batch was warmed to ambient temperature, aged for four hours and then cooled to −20° C. A solution of 2-(3-bromopropyloxy)-tetrahydropyan (850.0 g, s3.81 mol) in dry THF (450 mL) was added slowly via an addition funnel, maintaining the batch temperature at ≦−5° C., and then the batch was aged at ambient temperature overnight. Ice water (3 L) was added and the mixture was extracted with ethyl acetate (1×2 L, 1×1.5 L, 1×1 L). The combined organic layers were washed with water (4 L) and then concentrated to give ~874 g of crude 1-3 as an oil, which is used directly in the next step.

To a solution of crude 1-3 (873 g) in ethanol (3.5 L) was added a solution of HCl gas (278 g, 7.61 mol) in ethanol (2.5 L). The mixture was stirred at ambient temperature for 3 h, then concentrated under vacuum. The resulting oil was dissolved in warm isopropanol (700 mL) and ethanol (50 mL), then with mechanical stirring isopropyl acetate (1.2 L) was added slowly. The mixture was aged for 18 h at ambient temperature, cooled (with ice water) and filtered under nitrogen. The filter cake was washed with isopropyl acetate (3×500 mL) and vacuum-dried under nitrogen to give ~280 g of 1-4.

To a mixture of compound 1-4 (280 g) in dry THF (2 L) was added slowly a solution of triethylamine (166 g, 1.64 mol) in THF (400 mL). The mixture was stirred for 2 h, filtered and the filter cake (triethylamine hydrochloride) was washed with THF (2×500 mL). The filtrate was evaporated to dryness under vacuum to give 200 g compound 1-5 in 40% overall yield from 4-picoline. 1-4: mp 153°–154° C.; MS(CI) m/z 151 (M+-HCl).

$^1$H NMR (CD$_3$OD) δ 1.63 (m, 2H), 1.89 (m, 2H), 2.99 (t, J=7.8 Hz, 2H), 3.60 (t, J=6.2 Hz, 2H), 7.98 (d, J=6.5 Hz, 2H), 8.72 (d, J=6.5 Hz, 2H);

$^{13}$C NMR (CD$_3$OD) δ 27.3, 32.9, 36.7, 62.2, 128.6, 142.1, 166.6. Anal. Calcd for C$_9$H$_{14}$NOCl: C, 57.60; H, 7.52; N, 7.46; Cl, 18.89. Found: C, 57.65; H, 7.34; N, 7.33; Cl, 19.17.

Preparation of N-(n-Butanesulfonyl)-O-(4-(4-pyridinyl)butyl)-(L)-tyrosine (1-8)

To a dry 5 L three-neck round bottom flask equipped with a mechanical stirrer, nitrogen inlet and a thermometer probe containing a solution of N-n-butanesulfonyl-(L)-tyrosine methyl ester (400.3 g, 1.268 mol) and triphenylphosphine (417.5 g, 1.595 mol) in THF (600 mL)

was slowly added a solution of 4-(4-pyridinyl)-butanol (207.0 g, 1.37 mol) and diisopropyl azodicarboxylate (319.9 g, 1.582 mol) in THF (475 mL) via a 1-L addition funnel over 3.5 h. The temperature was maintained at 23°-26° C. using a water bath. The mixture was allowed to stir for additional 30 min, then hexane (1.1 L) and methylene chloride (60 mL) were added. The resulting mixture was loaded onto sand (1 kg, on top)/Silica Gel 60 (3 kg) in a 5 L sintered glass funnel, eluted with 1:1 hexanes/THF (32 L), and collected 2-L fractions. Fractions 1-8 were combined and the precipitate Ph$_3$PO was filtered. The filter cake was washed with 1:1 hexanes/THF (300 mL). The filtrate was concentrated to give 1051 g of crude methyl ester 1-7 as an oil.

To a solution of 1-7 (1051 g) in THF/MeOH/H$_2$O (3:1:1, 5 L) was added slowly solid LiOH.H$_2$O (108.5 g, 2.58 mol) at 25°-29° C. over 30 min. The mixture was aged for 1.5 h and then quenched by adding DI water (4 L) and conc. HCl (125 mL) to give a final pH 10.4. The mixture was diluted with water (4 L) and extracted with isopropyl acetate (4×3 L) and the combined organic layer was back-extracted with 0.1N NaOH (3 L). The combined aqueous layer was acidified to pH 4.5 using conc. HCl (100 mL) and then extracted with methylene chloride (3×4 L). The methylene chloride extracts were filtered through sand (1 kg, on top)/Silica Gel 60 (3 kg) in a 5 L sintered glass funnel, then eluted with ethyl acetate (4 L), ethyl acetate/methanol/acetic acid (12 L/0.6 L/60 mL) and ethyl acetate/methanol/acetic acid (28.1 L/3.5 L/350 mL), and collected in 4-L fractions. The product-enriched fractions 4–8 were combined and evaporated to dryness to give 466 g wet solid. The solid was recrystallized from isopropyl alcohol (6 L) by warming to 50° C. first and then cooling slowly to ambient temperature with stirring overnight. The slurry was filtered, washed with isopropyl alcohol (2×200 mL) and air-dried to give 305 g (55%) of 1-8. HPLC Assay: product 1-8, 99.5% area; RT=6.76 min; Zorbax RX-C8 column, 4.6 mm×25 cm ID; 220 nm; 1.5 mL/min; linear gradient 10 to 90% A over 10 min, A=CH$_3$CN, B=0.1% aqueous H$_3$PO$_4$.

mp 137°-138° C.; $[\alpha]^{25}_D = -14.7°$ (c 0.91, MeOH); MS(CI) m/z 435 (MH+).

$^1$H-NMR (CD$_3$OD) δ 0.86 (t, J=7.3 Hz, 3H), 1.33 (hex, J=7.3 Hz, 2H), 1.68 (m, 2H), 1.83 (m, 2H), 2.82 (m, 2H), 3.06 (A of ABX, J$_{AB}$=13.9 Hz, J$_{AX}$=6.3 Hz, 1H), 3.16 (B of ABS, J$_{BA}$=13.9 Hz, J$_{BX}$=5.0 Hz, 1H), 3.90 (t, J=5.7 Hz, 2H), 4.32 (X of ABX, J$_{XA}$=6.3 Hz, J$_{XB}$=5.0 Hz, 1H), 6.72 (d, J=8.6 Hz, 2H), 7.17 (d, J=8.6 Hz, 2H), 7.33 (d, J=6.3 Hz, 2H), 8.49 (d, J=6.3 Hz, 2H);

$^{13}$C-NMR (CDCl$_3$) δ 13.5, 21.5, 25.4, 26.5, 28.6, 35.1, 38.9, 53.0, 57.9, 67.0, 114.3, 125.0, 128.7, 130.8, 145.9, 155.8, 157.7, 175.0;

Anal. Calcd for C$_{22}$H$_{30}$O$_5$SN$_2$: C, 60.81; H, 6.96; N, 6.45; S, 7.38. Found: C, 60.53; H, 6.88; N, 6.26; S, 7.65.

Preparation of N-(n-butanesulfonyl)-O-(4-(4-piperidinyl)butyl)-(L)-tyrosine, hydrochloride, monohydrate (1-9)

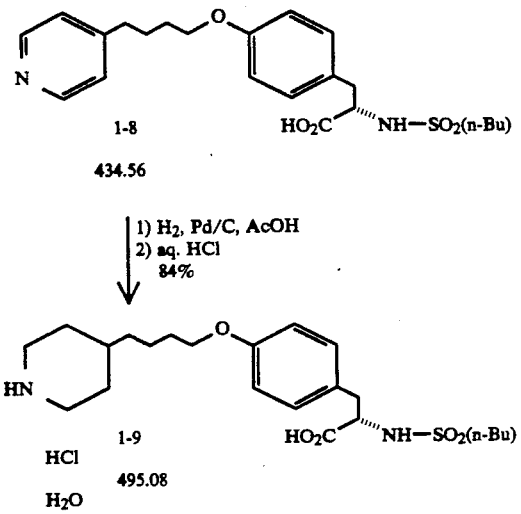

Pyridine 1-8 (274.6 g, 0.632 mol) and 10% Pd/C (27.5 g, 10 wt %) in acetic acid (2.75 L) was hydrogenated in a stainless steel vessel at 40 psi and 70° C. until complete uptake of hydrogen was observed (4–6 h). The reaction mixture was filtered through a pad of Solka-Flock (280 g; prewashed with 1 L acetic acid) and then washed with acetic acid (1 L). The filtrate was concentrated to a thick oil containing approximately 285 g acetic acid, then DI water (4.125 L) was added to give a concentration of 1 g/15 mL 7% acetic acid in water and the resulting slurry was stirred at 50° C. for 1 hour and at ambient temperature for 18 hours. The solid was collected on a sintered glass funnel, washed with DI water (3×350 mL) and dried under vacuum with nitrogen sweep to give 238.4 g (86%) of free base of 1-9 as a white solid.

HPLC Assay: free base of 1-9, 99.5 area %, RT=6.94 min; Zorbax RX-C8 column, 4.6 mm×25 cm ID; 220 nm; 1.5 mL/min; linear gradient 20 to 70% A over 12 min, A=CH$_3$CN, B=0.1% aqueous H$_3$PO$_4$. mp 223°-225° C.; $[\alpha]^{25}_D = -14.7°$ (c 0.91, MeOH).

$^1$H-NMR (CD$_3$OD) δ 0.88 (t, J=7.3 Hz, 3H), 1.33 (m, 6H), 1.58 (m, 5H), 1.76 (m, 2H), 1.81 (m, 2H), 2.77 (t, J=7.5, 2H), 2.80 (m, 1H), 2.88 (m, 2H), 3.03 (B of ABX, J$_{BA}$=13.9 Hz, J$_{BX}$=4.6 Hz, 1H), 3.30 (m, 2H), 3.90–4.0 (m, 3H), 6.80 (d, J=8.5 Hz, 2H), 7.18 (d, J=8.5 Hz, 2H). Anal. Calcd for C$_{22}$H$_{37}$O$_5$N$_2$S: C, 59.84; H, 8.40; N, 6.34; S, 7.24. Found: C, 59.98; H, 8.40; N, 6.40; S, 7.24.

To a rapidly stirred suspension of free base of 1-9 (24.64 g, 55.93 mol) and isopropyl acetate (1 L) was added concentrated hydrochloric acid (10 mL) dropwise. The temperature remained at 19° C. throughout addition. The mixture was then stirred at room temperature (19° C.) for a further 6 hours. The product was isolated by filtration under nitrogen. The solid product was washed with isopropyl acetate (2×100 mL) and suction-dried under nitrogen overnight to afford 27.1 g (98%) of 1-9.

HPLC Assay: 1-9, 99.8 area %; RT=6.79 min; Zorbax RX-C8 column, 4.6 mm×25 cm ID; 220 nm; 1.5 mL/min; linear gradient 10 to 90% A over 10 min, A=CH$_3$CN, B=0.1% aqueous H$_3$PO$_4$; or 1-9, 99.8 area %, RT=6.94 min; Zorbax RX-C8 column, 4.6 mm×25 cm ID; 220 nm; 1.5 mL/min; linear gradient 20 to 70% A over 12 min, A=CH₃CN, B=0.1% aqueous H₃PO₄.

Chiral HPLC: L-isomer, >99.9%; RT=10 min; D-isomer, <0.1%; RT=8.5 min; ULTRON-ES-OVM column, 4.6 mm×25 cm, 5 m, with guard column; 270 nm; 0.7 mL/min; isocratic, 90% Buffer (6 g ammonium formate adjusted to pH 4.1 with formic acid), 10% MeOH. mp1 87°-88° C., mp2 131°-132° C.; $[\alpha]^{25}_D = -14.4°$ (c 0.92, MeOH);

¹H-NMR (CD₃OD) δ 0.84 (t, J=7.3 Hz, 3H), 1.23 (hex, J=7.3 Hz, 2H), 1.30-1.70 (m, 9H), 1.75 (m, 2H), 1.95 (m, 2H), 2.64 (t, J=7.4, 2H), 2.77 (A of ABX, $J_{AB}$=13.9 Hz, $J_{AX}$=9.8 Hz, 1H), 2.95 (m, 2H), 3.11 (B of ABX, $J_{BA}$=13.9 Hz, $J_{BX}$=4.6 Hz, 1H), 3.47 (m, 2H), 3.95 (t, J=6.2 Hz, 2H), 4.09 (X of ABX, $J_{XA}$=9.8 Hz, $J_{XB}$=4.6 Hz, 1H), 6.84 (d, J=8.6 Hz, 2H), 7.18 (d, J=8.6 Hz, 2H).

¹³C-NMR (CD₃OD) δ 14.0, 22.5, 24.0, 26.5, 30.0, 30.4, 34.8, 36.8, 39.0, 45.3, 54.1, 59.4, 68.7, 115.5, 130.4, 131.7, 159.6, 175.2.

IR (Nujol, cm⁻¹) 3520, 3208, 3166, 2800-2300, 1727, 1610, 1595, 1324, 1256, 1141, 1119, 829.

HRMS calcd for C₂₂H₃₇N₂O₅S 441.2423, found 441.2423 (M+—H₂O—HCl). Anal. Calcd for C₂₂H₃₉O₆ClN₂S: C, 53.37; H, 7.94; N, 5.66; Cl, 7.16; S, 6.48. Found: C, 53.56; H, 8.04; N, 5.62; Cl, 7.36; S, 6.53.

What is claimed is:

1. A process for preparing compounds of the following formula:

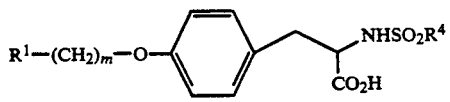

wherein:
R¹ is a six member saturated or unsaturated heterocyclic ring containing one or two heteroatoms wherein the heteroatoms are N; or NR⁶, wherein R⁶ is C₁₋₁₀ alkyl;
m is an integer from two to six; and
R⁴ is aryl, C₁₋₁₀ alkyl, or C₄₋₁₀ aralkyl,
according to the process steps whereby

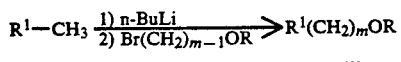

methylated R¹ is reacted with nBuLi, before quenching with a straight chain alkyl group having Br at one end and OR at the other end, to yield (2), wherein R is tetrahydropyran;

(2) is aged, first in hydrogen chloride gas in ethanol, and then neutralized in triethylamine/tetrahydrofuran and to yield (3); and

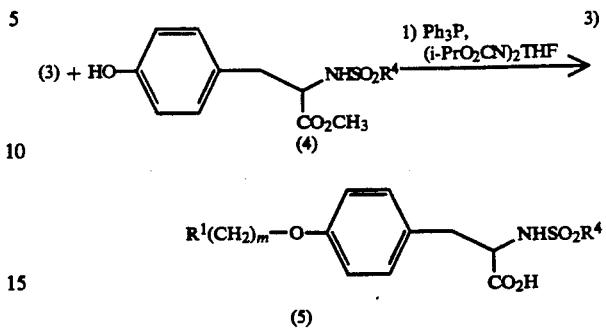

a solution of (4) and Ph₃P in THF is combined with (3) and (iPrO₂CN)₂ in THF to yield (5) after ester hydrolysis.

2. A process according to claim 1, wherein a compound of the formula

wherein R¹ is a six membered unsaturated heterocyclic ring containing one or two N heteroatoms,
is selectively hydrogenated using Pd/C in acetic acid to yield

wherein R² is a six membered saturated heterocyclic ring containing one or two N heteroatoms.

3. A process according to claim 2, wherein m is 4;

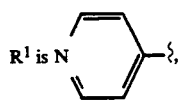

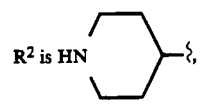

and

* * * * *